(12) United States Patent
Bahmer et al.

(10) Patent No.: US 9,398,382 B2
(45) Date of Patent: *Jul. 19, 2016

(54) AUDITORY PROSTHESIS STIMULATION RATE AS A MULTIPLE OF INTRINSIC OSCILLATION

(71) Applicant: MED-EL Elektromedizinische Geraete GmbH, Innsbruck (AT)

(72) Inventors: Andreas Bahmer, Aschaffenburg (DE); Peter Schleich, Telfs (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 15 days.

This patent is subject to a terminal disclaimer.

(21) Appl. No.: 14/461,506

(22) Filed: Aug. 18, 2014

(65) Prior Publication Data

US 2015/0051669 A1 Feb. 19, 2015

Related U.S. Application Data

(60) Provisional application No. 61/867,200, filed on Aug. 19, 2013, provisional application No. 62/006,946, filed on Jun. 3, 2014.

(51) Int. Cl.
*A61N 1/36* (2006.01)
*H04R 25/00* (2006.01)
*A61N 1/05* (2006.01)

(52) U.S. Cl.
CPC .......... *H04R 25/505* (2013.01); *A61N 1/36032* (2013.01); *A61N 1/0541* (2013.01)

(58) Field of Classification Search
CPC ................. A61N 1/0541; A61N 1/36032
See application file for complete search history.

(56) References Cited

U.S. PATENT DOCUMENTS

| | | | |
|---|---|---|---|
| 6,035,271 | A | 3/2000 | Chen |
| 6,829,578 | B1 | 12/2004 | Huang et al. |
| 7,043,430 | B1 | 5/2006 | Chung et al. |
| 7,920,923 | B2 | 4/2011 | Laback et al. |
| 2003/0088402 | A1 | 5/2003 | Hoory et al. |

(Continued)

FOREIGN PATENT DOCUMENTS

WO  WO 02/096153  11/2002  ............. H04R 25/00

OTHER PUBLICATIONS

Bronkhorst, et al, "The effect of head-induced interaural time and level differences on speech intelligibility in noise", J. Acoust. Soc. Am, vol. 83, No. 4, Apr. 1988, pp. 1508-1516, 9 pages.

(Continued)

*Primary Examiner* — Eric D. Bertram
(74) *Attorney, Agent, or Firm* — Sunstein Kann Murphy & Timbers LLP

(57) ABSTRACT

A method is described for generating electrical stimulation signals for stimulation contacts in an auditory implant system. Characteristic feature periods are determined for frequency components in an input audio signal. For selected feature periods that meet a period selection criteria, adjusted feature periods are determined that correspond to a nearest integer multiple of a language-specific fundamental period. A corresponding stimulation rate frequency is determined for each adjusted feature period, and each stimulation rate frequency is assigned to one or more stimulation contacts. The stimulation signals are then generated for the stimulation contacts at their respective stimulation rate frequencies.

14 Claims, 9 Drawing Sheets

(56) References Cited

U.S. PATENT DOCUMENTS

| | | | |
|---|---|---|---|
| 2005/0271222 | A1 | 12/2005 | Freed et al. |
| 2006/0247735 | A1 | 11/2006 | Honert |
| 2009/0312820 | A1 | 12/2009 | Nie et al. |
| 2011/0286618 | A1* | 11/2011 | Vandali et al. ............ 381/320 |

OTHER PUBLICATIONS

Buell, et al, "Discrimination of interaural differences of time in the envelopes of high-frequency signals: Integration times", *J. Acoust. Soc. Am.*, vol. 84, No. 6, Dec. 1988, pp. 2063-2066, 4 pages.

Colburn, et al, "Binaural Directional Hearing—Impairments and Aids", *Directional Hearing*, 1987, pp. 261-278.

Durlach, et al, "Binaural Interaction in Impaired Listeners", *Audiology*, 20: (1981), pp. 181-211, 31 pages.

Gabriel, Kaigham J., "Frequency dependence of binaural performance in listeners with impaired binaural hearing", *J. Acoust. Soc. Am*, vol. 91, No. 1, Jan. 1992, pp. 336-347, 12 pages.

Hafter, et al, "Detection of interaural differences of time in trains of high-frequency clicks as a function of interclick interval and number", *J. Acoust. Soc. Am*, vol. 73, No. 2, Feb. 1983, pp. 644-651, 8 pages.

Hawkins, et al, "Interaural Time Discrimination Ability of Listeners with Sensorineural Hearing Loss", *Audiology*, vol. 19, (1980), pp. 495-507, 13 pages.

Kaibao, N., et al, "Encoding Frequency Modulation to Improve Cochlear Implant Performance in Noise", *IEEE Transactions on Biomedical Engineering*, vol. 52, No. 1, Jan. 2005, pp. 64-73, 10 pages.

Koehnke, et al, "Effects of Reference Interaural Time and Intensity Differences on Binaural Performance in Listeners with Normal and Impaired Hearing", *Ear & Hearing*, vol. 16, No. 4, pp. 331-353, 23 pages.

Koehnke, et al, "Binaural Performance in Listeners With Impaired Hearing: Aided and Unaided Results", *Binaural and spatial Hearing in Real and Virtual Environments*, R. Gilkey 7 T. Anderson eds., Erlbaum, Hillsdale, NJ, Chapter 33, pp. 725-751, 14 pages.

Laback, et al, "Binaural jitter improves interaural time-difference sensitivity of cochlear implantees at high pulse rates", *PNAS*, vol. 105, No. 2., Jan. 15, 2008, pp. 814-817, 4 pages.

Laback, et al, "Lateralization discrimination of interaural time delays in four-pulse sequences in electric and acoustic hearing", *J. Acoust. Soc. Am*, vol. 121, No. 4, Apr. 2007, pp. 2182-2191, 10 pages.

Litvak, et al, "Auditory nerve fiber responses to electric stimulation: Modulated and unmodulated pulse trains", *J. Acoust. Soc. Am*, vol. 110, No. 1, Jul. 2001, pp. 368-379, 12 pages.

Macpherson, et al, "Listener weighting of cues for lateral angle: The duplex theory of sound localization revisited", *J. Acoust. Soc. Am*, vol. 111, No. 5, Pt. 1, May 2002, pp. 2219-2236, 18 pages.

Majdak, et al, "Effects of interaural time differences in fine structure and envelope on lateral discrimination in electric hearing", *J. Acoust. Soc. Am*, vol. 120, No. 4, Oct. 2006, pp. 2190-2201, 12 pages.

Saberi, Kourosh, "Observer weighting of interaural delays in filtered impulses", *Perception & Psychophysics*, 58, (7), 1996, pp. 1037-1046, 10 pages.

Smith, et al, "Chimaeric sounds reveal dichotomies in auditory perception", *Nature*, Mar. 7, 2002; 416(6876), pp. 87-90, 10 pages.

Smoski, et al, "Discrimination of interaural temporal disparities by normal-hearing listeners and listeners with high-frequency sensorineural hearing loss", *J. Acoust. Soc. Am.*, vol. 79, No. 5, May 1986, pp. 1541-1547, 7 pages.

Stecker, G. C., et al, "Temporal weighting in sound localization", *J. Acoust. Soc. Am*, vol. 122, No. 3, Pt. 1, Sep. 2002, pp. 1046-1057, 12 pages.

Van Hoesel, et al, "Speech perception, localization and laterization with bilateral cochlear implants", *J. Acoust. Soc. Am*. vol. 113, No. 3, Mar. 2003, pp. 1617-1630, 14 pages.

Van Hoesel, Richard J. M., "Sensitivity to binaural timing in bilateral cochlear implant users", *J. Acoust. Soc. Am*, vol. 121, No. 4, Apr. 2007, pp. 2192-2206, 15 pages.

Wightman, et al, "Factors Affecting the Relative Salience of Sound Localization Cues", *Gikey and Anderson*, [20], 1997, Chapter 1, pp. 1-23, 23 pages.

Zeng, et al, "Speech recognition with amplitude and frequency modulations", *PNAS*, vol. 102, No. 7, Feb. 15, 2005, pp. 2293-2298, 6 pages.

International Searching Authority, Authorized Officer Dana Schalinatus, International Search Report and Written Opinion PCT/EP2008/004959, date of mailing Aug. 25, 2008, 14 pages.

International Searching Authority, Authorized Officer Shane Thomas, International Search Report and Written Opinion PC/US14/51412, date of mailing Dec. 9, 2014, 19 pages.

* cited by examiner

AUDITORY PROSTHESIS STIMULATION RATE AS A MULTIPLE OF INTRINSIC OSCILLATION

This application claims priority from U.S. Provisional Patent Application 61/867,200, filed Aug. 19, 2013, and from U.S. Provisional Patent Application 62/006,946, filed Jun. 3, 2014, which are incorporated herein by reference in their entireties.

FIELD OF THE INVENTION

The present invention relates to medical implants, and more specifically to electric stimulation techniques in cochlear implant systems and other implantable auditory prostheses.

BACKGROUND ART

A normal human ear transmits sounds as shown in FIG. 1 through the outer ear 101 to the tympanic membrane 102 which moves the bones of the middle ear 103 that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode can electrically stimulate auditory nerve tissue with small currents delivered by multiple electrode contacts distributed along the electrode. Although the following discussion is specific to cochlear implants, some hearing impaired persons are better served when the stimulation electrode is implanted in other anatomical structures. Thus auditory implant systems include brainstem implants, middle brain implants, etc. each stimulating a specific auditory target in the hearing system.

FIG. 1 also shows some components of a typical cochlear implant system where an external microphone provides an audio signal input to an external signal processor 111 in which various signal processing schemes can be implemented. For example, signal processing approaches that are well-known in the field of cochlear implants include continuous interleaved sampling (CIS) digital signal processing, channel specific sampling sequences (CSSS) digital signal processing (as described in U.S. Pat. No. 6,348,070, incorporated herein by reference), spectral peak (SPEAK) digital signal processing, fine structure processing (FSP) and compressed analog (CA) signal processing.

The processed signal is then converted into a digital data format for transmission by external transmitter coil 107 into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrode contacts 112 on its surface that provide selective stimulation of the cochlea 104.

FIG. 2 shows various functional blocks in a typical CI signal processing system using the CIS stimulation strategy. A sound pre-processor 201 includes a pre-emphasis filter 203 that receives an audio signal from a microphone and attenuates strong frequency components in the audio signal below about 1.2 kHz. The sound pre-processor 201 also includes multiple band-pass filters (BPFs) 204 that decompose the audio signal from the pre-emphasis filter 203 into multiple spectral bands. A sound processor 202 includes envelope detectors 205 that extract the slowly-varying envelopes of the spectral band signals, for example, by full-wave rectification and low pass filtering. The sound processor 202 also includes a non-linear (e.g., logarithmic) mapping module 206 that performs compression of the envelopes to fit the patient's perceptual characteristics, and the compressed envelope signals are then multiplied with carrier waveforms by modulators 207 to produce electric stimulation signals in the specific form of non-overlapping biphasic output pulses for each of the stimulation electrodes (EL-1 to EL-n) implanted in the cochlea reflecting the tonotopic neural response of the cochlea 104 along the length of the implanted electrode array 110.

CIS stimulation imposes a fixed stimulation rate on the delivered electrical pulses and therefore cannot represent periodicity components of the sensed audio signal. On the other hand, FSP stimulation (and its variants) does represent the inherent periodicity of sensed audio signals. FSP generates stimulation pulse trains responsive to detection of specific pre-defined signal characteristics such as zero crossing events. But FSP pulse trains after zero crossing events can only be presented in a pre-defined pattern. That means that the time period between the actual zero crossing and the initial pulse of the pulse trains may be different for each zero crossing event, thereby introducing unwanted jitter. In contrast to the case of unwanted signal jitter, U.S. Pat. No. 7,920,923 describes intentionally introducing a random artificial phase jitter component to binaural stimulation signals. This is done to reduce the periodic characteristics of the fine structure component while preserving interaural time difference (ITD) information.

In the specific case of speech in a tonal language, auditory implant stimulation schemes have further additional considerations. Tonal languages are characterized in that a given spoken syllable will have a different meaning depending on its pitch characteristics. For a simplified example, the pitch contours of the four tones of Chinese Mandarin speech are shown in FIG. 3. Tone 1 (T1) has a nearly constant pitch, tone 2 (T2) has pitch that is mostly rising, tone 3 (T3) has pitch that falls and rises, and tone 4 (T4) has pitch that is mostly falling. If pronounced as [ma:], T1 means 'mother', T2 means 'hemp', T3 means 'horse' and T4 means 'to grumble'. Depending on whether that syllable is spoken by a male, female, or a child, the distance between the horizontal lines on FIG. 3 will typically be 1.2, 0.8 or 0.4 milliseconds.

Pitch is encoded predominantly in the temporal structure of the signal, the fundamental frequency F0 and higher harmonics. FIG. 4 shows narrowband spectrograms and F0 contours of the four tone patterns of "shi" spoken by a female subject where the grayscale indicates energy associated with time (x-axis) and frequency (y-axis), and the thick black lines represent the F0 contours extracted by autocorrelation.

SUMMARY OF THE INVENTION

Embodiments of the present invention are directed to arrangements for generating electrical stimulation signals for stimulation contacts in an auditory implant system. Characteristic feature periods are determined for frequency components in an input audio signal. For selected feature periods that meet a period selection criteria, adjusted feature periods are determined that correspond to a nearest integer multiple of a language-specific fundamental period. A corresponding stimulation rate frequency is determined for each adjusted feature period, and each stimulation rate frequency is assigned to one or more stimulation contacts. The electrical stimulation signals are then generated for the stimulation contacts at their respective stimulation rate frequencies.

The input audio signal may be processed using a band pass filter bank to produce a plurality of band pass frequency signals, in which case characteristic feature periods are determined for each of the band pass frequency signals. In addition or alternatively, the input audio signal may be processed using a Fast Fourier Transformation. The frequency components may be fundamental frequency components and/or harmonic frequency components of the input audio signal. The language-specific fundamental period may be characteristic of a tonal language, for example, 0.4 milliseconds as in Chinese Mandarin.

Embodiments of the present invention also are directed are directed to generating electrical stimulation signals for the stimulation contacts on an outer surface of an implanted electrode array. An input audio signal is pre-processed to produce multiple representative frequency band signals each having a prominent sensed frequency. Each of the frequency band signals is then processed to generate corresponding electric stimulation signals for the stimulation contacts. Each of the electric stimulation signals has an associated stimulation frequency, and for at least one of the electric stimulation signals, the stimulation frequency is varied to maintain an integer ratio between the stimulation frequency and the prominent sensed frequency of the corresponding frequency band signal.

In specific embodiments, the frequency band signals may be produced by a bank of band pass filters each associated with a corresponding audio frequency band. For each of the electric stimulation signals, the stimulation frequency may be varied to maintain an integer ratio between the stimulation frequency and the sensed frequency of the corresponding frequency band signal.

The prominent sensed frequency of the band pass signal associated with the selected at least one electric stimulation signal may be a fundamental frequency and/or a harmonic of a fundamental frequency of the band pass signal. Or the prominent sensed frequency of the band pass signal associated with the selected at least one electric stimulation signal may be a most prominent frequency of the band pass signal. The prominent sensed frequency may be determined using a fast Fourier transform.

In specific applications, the stimulation frequency may be varied as a function of a music processing mode and/or a target audio source processing mode of the auditory prosthesis system.

DETAILED DESCRIPTION OF SPECIFIC EMBODIMENTS

Analysis of pitch contours shows that speakers of tonal languages tend to resolve pitch steps in increments that are integer multiples of a language-specific fundamental period. In the specific case of Chinese Mandarin, this language-specific fundamental period is found to be 0.4 msec and the resulting pitch increments are integer multiples of that fundamental period, namely 0.4, 0.8 or 1.2 msec etc. In addition, other psychophysical and electrophysiological results show that a period of 0.4 msec is also the basis for intrinsic oscillations in the auditory system. Interestingly, this 0.4 msec fundamental pitch period seems to be not only a relative difference in the speech of just a single speaker, but rather is embedded in an absolute pitch grid of possible fundamental frequencies F0 across many different speakers.

Figure 1:
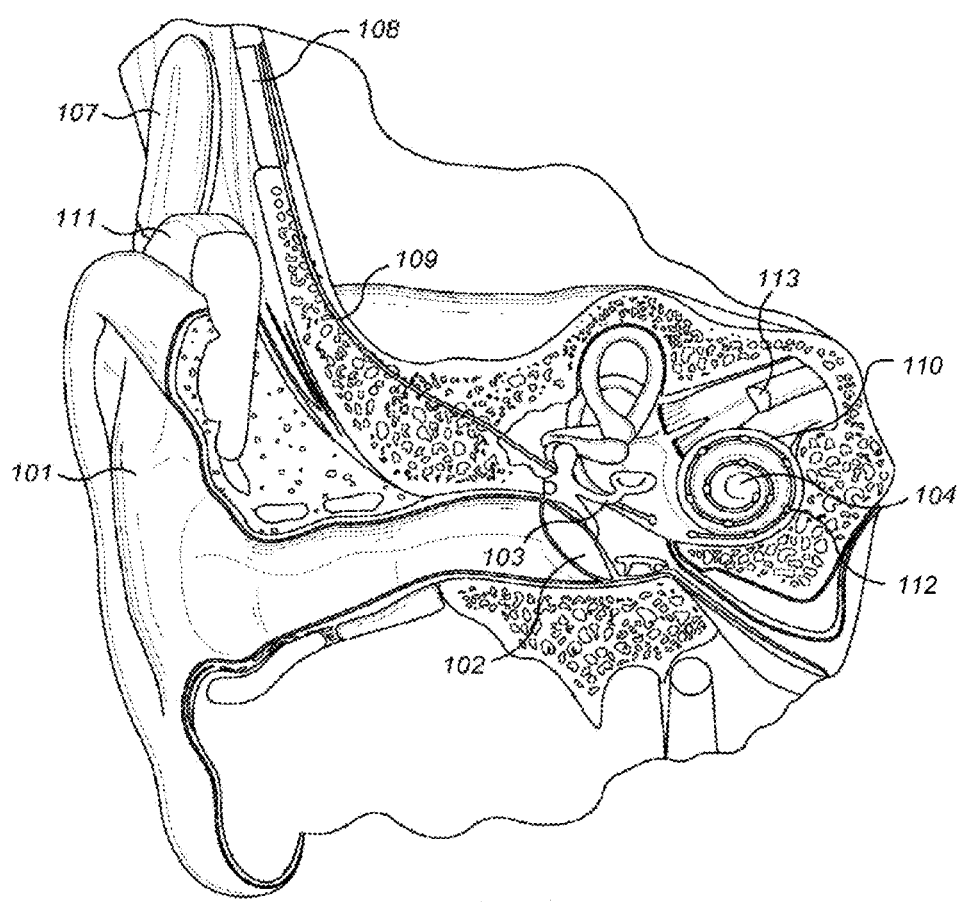
FIG. 1 shows a section view of a human ear with a typical auditory prosthesis system designed to deliver electric stimuli to the inner ear and acoustic stimuli at the ear canal.
Figure 2:
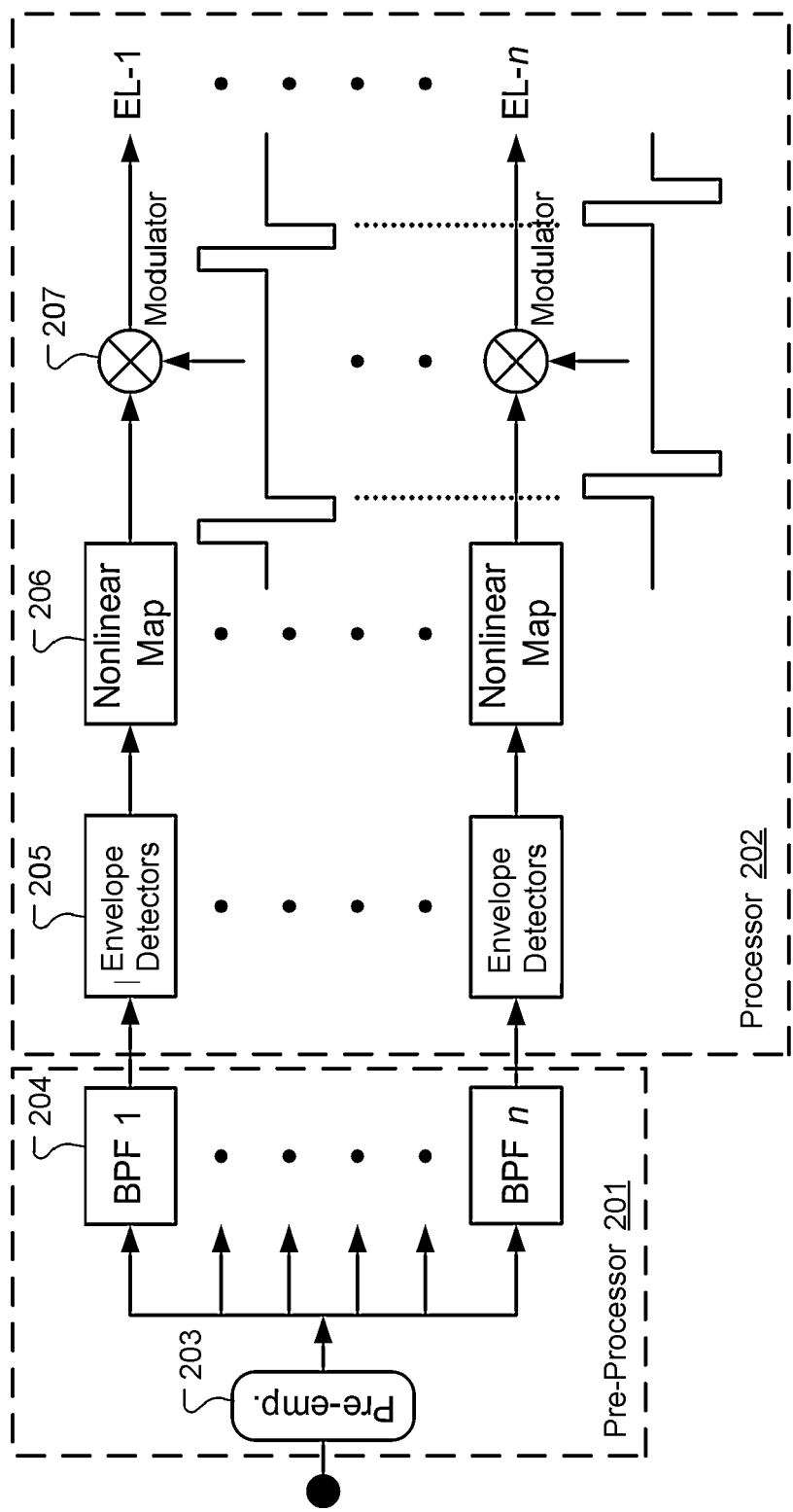
FIG. 2 shows various functional blocks in a continuous interleaved sampling (CIS) processing system.
Figure 3:
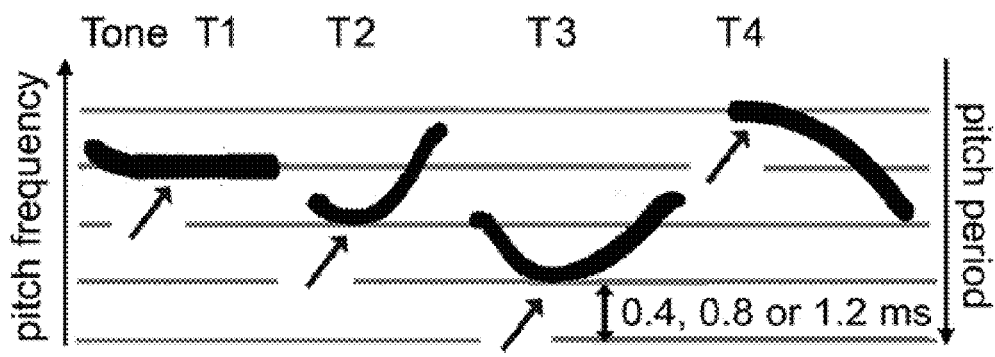
FIG. 3 shows pitch contours for the four tones in Chinese Mandarin speech.
Figure 4:
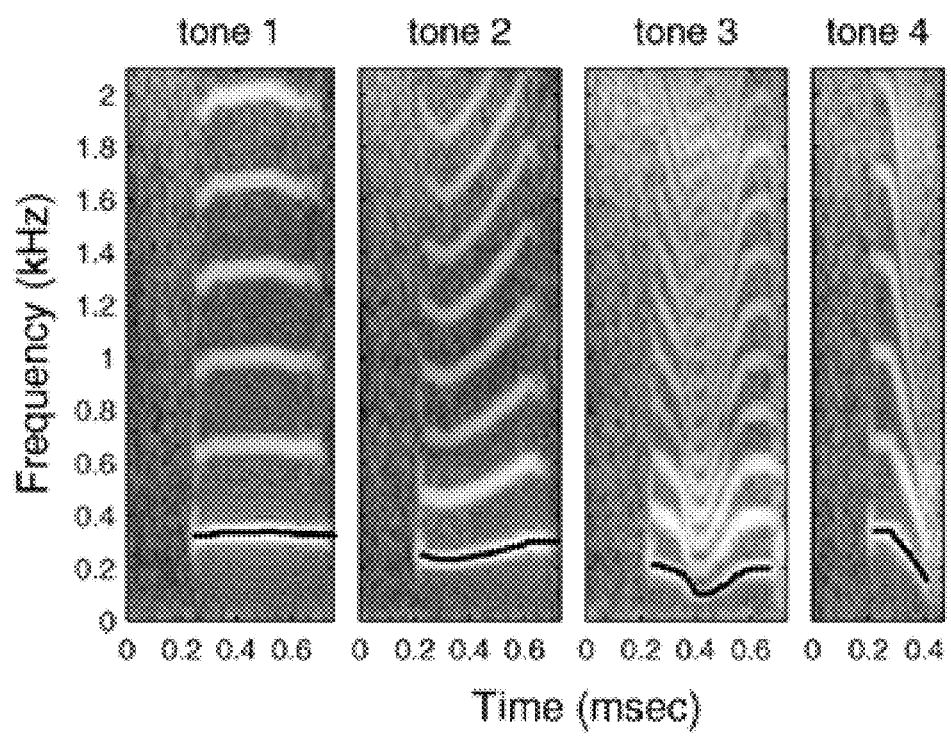
FIG. 4 shows narrowband spectrograms and F0 contours for the four tones of "shi" by a female speaker.
Figure 5:
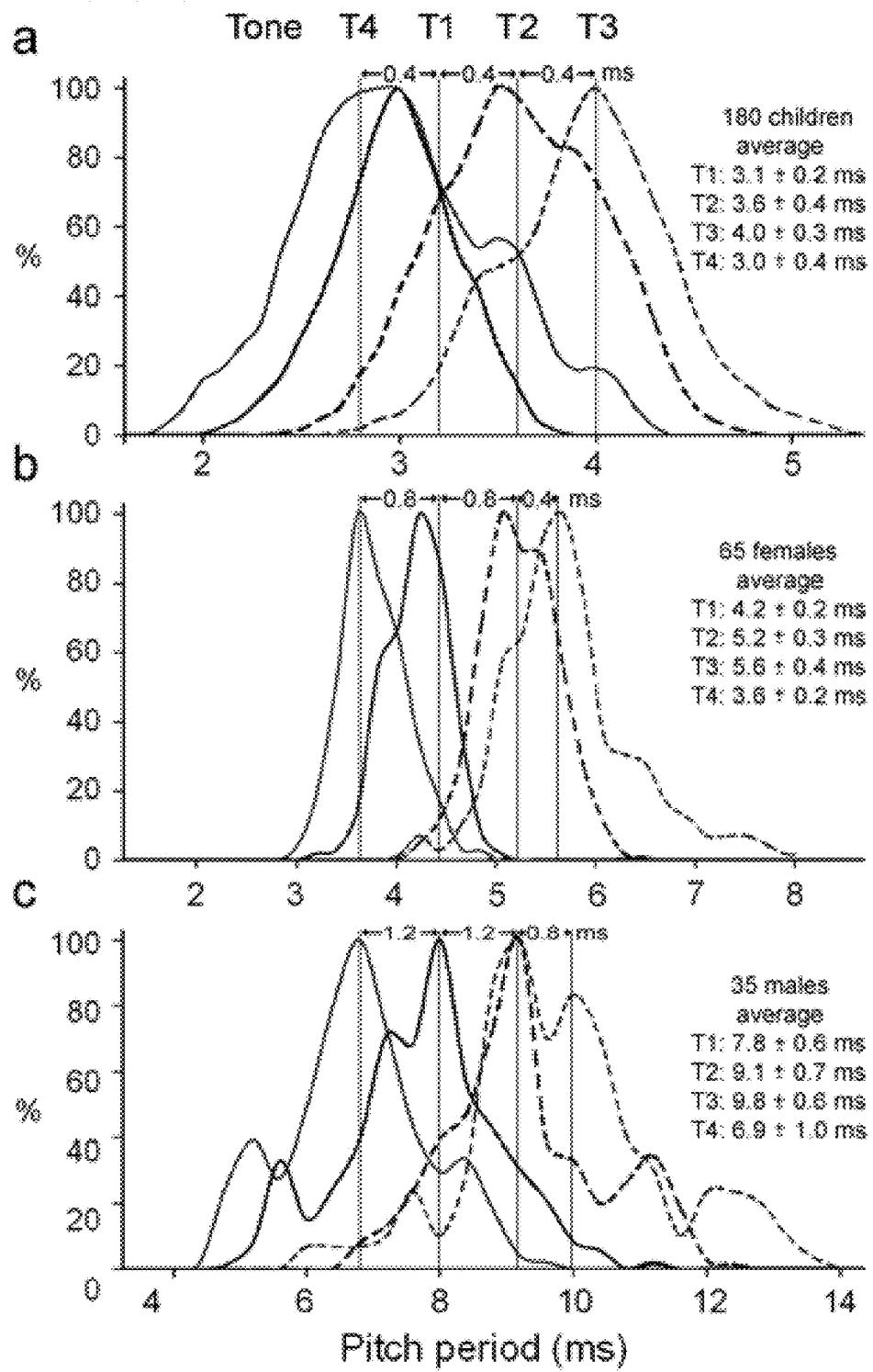
FIG. 5 shows pitch distribution data of the four Mandarin tones for many speakers.

FIG. 5 shows pitch distribution data of the four Mandarin tones (corresponding to the pitch levels indicated by the arrows) for many Mandarin speakers: 180 children, 56 female and 35 male speakers. Among all three of those groups, strong peaks corresponding to the characteristic pitches of the different tones are visible. For all three groups shown in FIG. 5, tone T4 is on the left, followed by T1, T2, and T3 (compare with FIG. 3). FIG. 5 also shows some side peaks that indicate a high degree of correlation with the 0.4 msec grid.

Existing stimulation strategies do not account for a language-specific fundamental period in tonal languages such as the 0.4 msec fundamental pitch period found in Chinese Mandarin. The adjustment of the electrical stimulation rate of the auditory prosthesis system to this language-specific fundamental period may improve the ability of implanted patients to understand and speak tonal languages by being able to better differentiate between pitch increments. Thus in Mandarin, the stimulation rate would be adjusted to an integer multiple of 0.4 msec that is related to nearest stable F0 determined in the pitch contour. This may help to improve speech understanding in Chinese Mandarin.

Figure 6A:
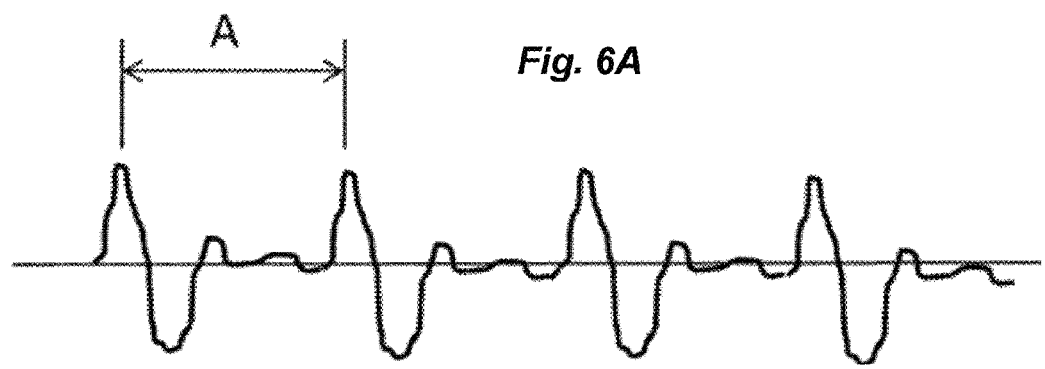
FIGS. 6A and 6B show pitch period characteristics for a broadband speech signal.
Figure 6B:
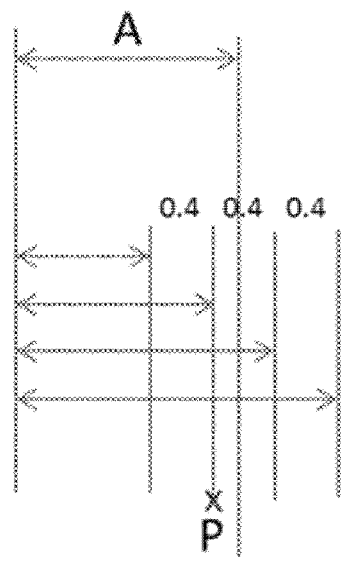

The basic approach can be described with regards to the broadband speech signal shown in FIG. 6A. From such a waveform signal, the fundamental frequency F0 can be determined. The dominant periodicity in the signal shown is indicated as A, so the fundamental frequency F0 is 1/A. Then as shown in FIG. 6B, the closest period P is determined that represents an integer multiple of the language-specific fundamental period, 0.4 msec. The electrical stimulation rate R is then defined as R=1/P. For a language-specific fundamental period of 0.4 msec, the possible stimulation rates (in Hz) are shown in the following table:

| ms | Hz |
| --- | --- |
| 0.4 | 2500 |
| 0.8 | 1250 |
| 1.2 | 833 |
| 1.6 | 625 |
| 2 | 500 |
| 2.4 | 417 |
| 2.8 | 357 |
| 3.2 | 313 |
| 3.6 | 278 |
| 4 | 250 |
| 4.4 | 227 |
| 4.8 | 208 |
| 5.2 | 192 |
| 5.6 | 179 |
| 6 | 167 |
| 6.4 | 156 |
| 6.8 | 147 |
| 7.2 | 139 |
| 7.6 | 132 |
| 8 | 125 |
| 8.4 | 119 |
| 8.8 | 114 |
| 9.2 | 109 |
| 9.6 | 104 |
| 10 | 100 |
| 10.4 | 96 |
| 10.8 | 93 |
| 11.2 | 89 |
| 11.6 | 86 |
| 12 | 83 |
| 12.4 | 81 |
| 12.8 | 78 |
| 13.2 | 76 |

(Note that higher harmonics may be represented by stimulation rates that are multiples of R). So for a male speaker having a fundamental frequency of 87 Hz, the stimulation rate R is determined as 86 Hz. The stimulation rate which represents the first harmonic would be 167 Hz (which is closest to 2 × 86 Hz = 172 Hz). The same approach can be applied to higher order harmonics of the fundamental frequency.

Figure 7:
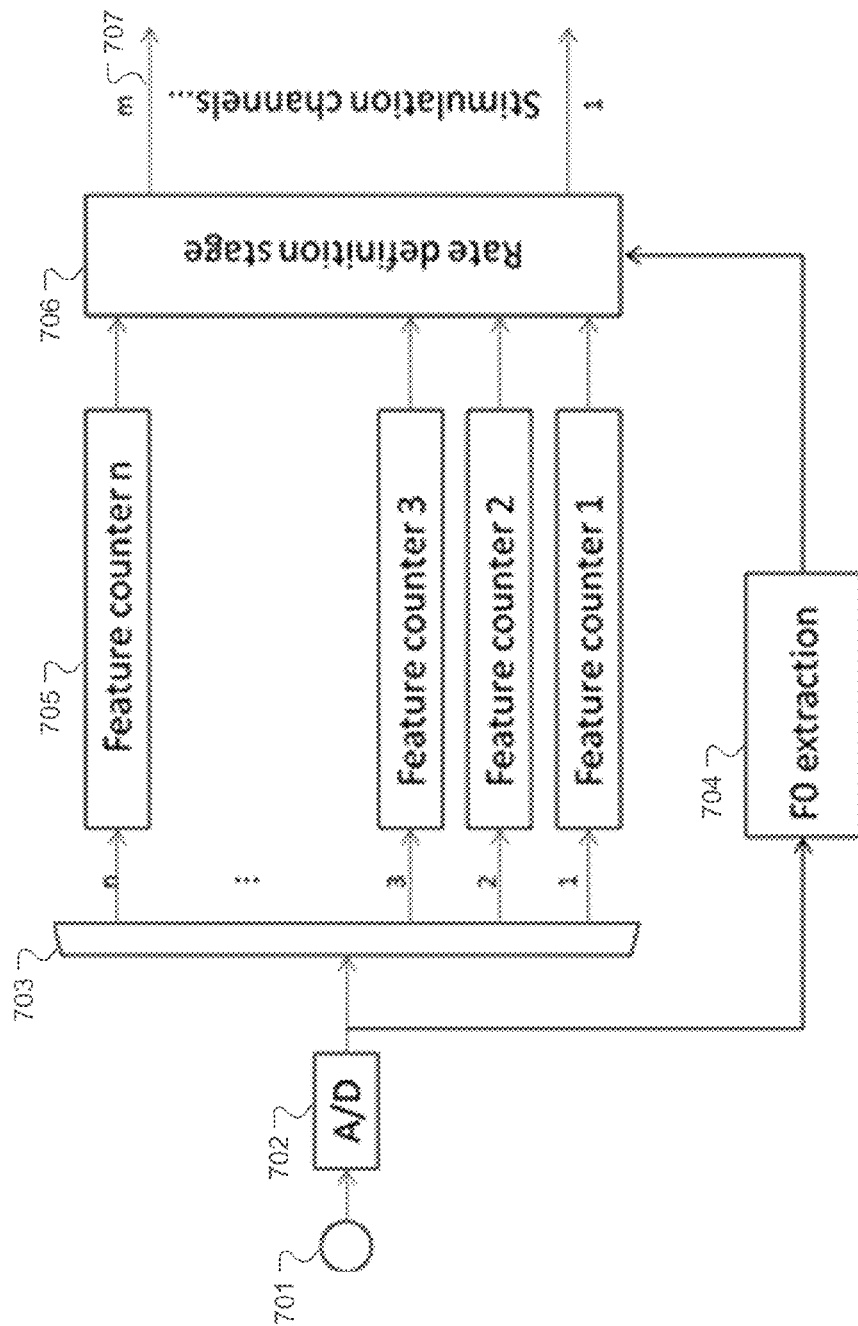
FIG. 7 shows various functional blocks in a feature extraction system in the time domain according to an embodiment of the present invention.

FIG. 7 shows various functional blocks in a feature extraction system for a cochlear implant that operates in the time domain according to an embodiment of the present invention. A microphone 701 detects ambient sound and converts it into a representative electrical microphone signal which an A/D conversion module 702 converts into a corresponding digital audio input signal. The digitized audio input signal is split and forwarded to both a band pass filter bank 703 that produces n band pass frequency signals, and a parallel F0 extraction module 704 that determines the fundamental frequency F0 of the input audio signal; for example, by an autocorrelation method. The feature counters 705 extract features of the n band pass frequency signals in the time domain. For example, the extracted frequency may specifically be zero crossing events, which are then forwarded to the rate definition stage 706. Also forwarded to the rate definition stage 706 is the extracted F0 frequency from the F0 extraction module 704. The rate definition stage 706 outputs electrical stimulation signals 707 to the stimulation contacts of an implanted electrode array for electrical stimulation adjacent neural tissue; e.g., a CI electrode array that stimulates neural tissue within the implanted cochlea.

More specifically with regards to the rate definition stage 706, it determines characteristic feature periods for frequency components in an input audio signal—that is, for the frequency features extracted by the feature counters 705. For selected feature periods that meet a period selection criteria, the rate definition stage 706 determines adjusted feature periods that correspond to a nearest integer multiple of a language-specific fundamental period. The period selection criteria may be based on periodic features that correspond to the fundamental frequency of the band pass frequency signal, resolved or unresolved harmonics, and/or any other periodic features present in the band pass signals. For example, a series of zero crossing events might be used as a periodic feature if the standard deviation of the time differences of subsequent zero crossing events or groups of zero crossing events are within a specific (e.g. predefined) value around the average of these time differences.

Specifically for Mandarin, the rate definition stage 706 determines adjusted feature periods that correspond to a nearest integer multiple of the 0.4 msec fundamental period. For each adjusted feature period, the rate definition stage 706 then assigns the corresponding stimulation rate frequency to one or more stimulation contacts 1 to m (m may or may not be equal to n, the number of band pass channels; e.g. n>m) on the implanted electrode array according to the frequency ranges of the tonotopic placement of the stimulation contacts within the cochlea. The rate definition stage 706 then generates the output electrical stimulation signals 707 for the stimulation contacts at their respective stimulation rate frequencies.

In some embodiments, the rate definition stage 706 determines adjusted feature periods where the periods of the selected frequency features are within some threshold distance of a nearest integer multiple of a language-specific fundamental period. Where the periods of selected frequency features are greater than that threshold distance from a nearest integer multiple of a language-specific fundamental period, the rate definition stage 706 may set the adjusted feature periods to zero (i.e., not used). In such embodiments, the rate definition stage 706 would then calculate the corresponding stimulation rate frequency only for adjusted feature periods other than zero.

If more than one non-zero feature frequency is assigned to a given stimulation contact channel, the rate definition stage 706 may select a single feature frequency out the assigned feature frequencies and provide output stimulation signals 707 at that stimulation rate. If only zero period feature frequencies have been applied to a given output stimulation channel (1 to m), no stimulation signal pulses are provided. In developing the output stimulation signals 707, the stimulation rate stage 706 also apply any appropriate stimulation strategy such as CIS, FSP, etc. and the output stimulation signals 707 may be provided in parallel or sequentially.

Figure 8:
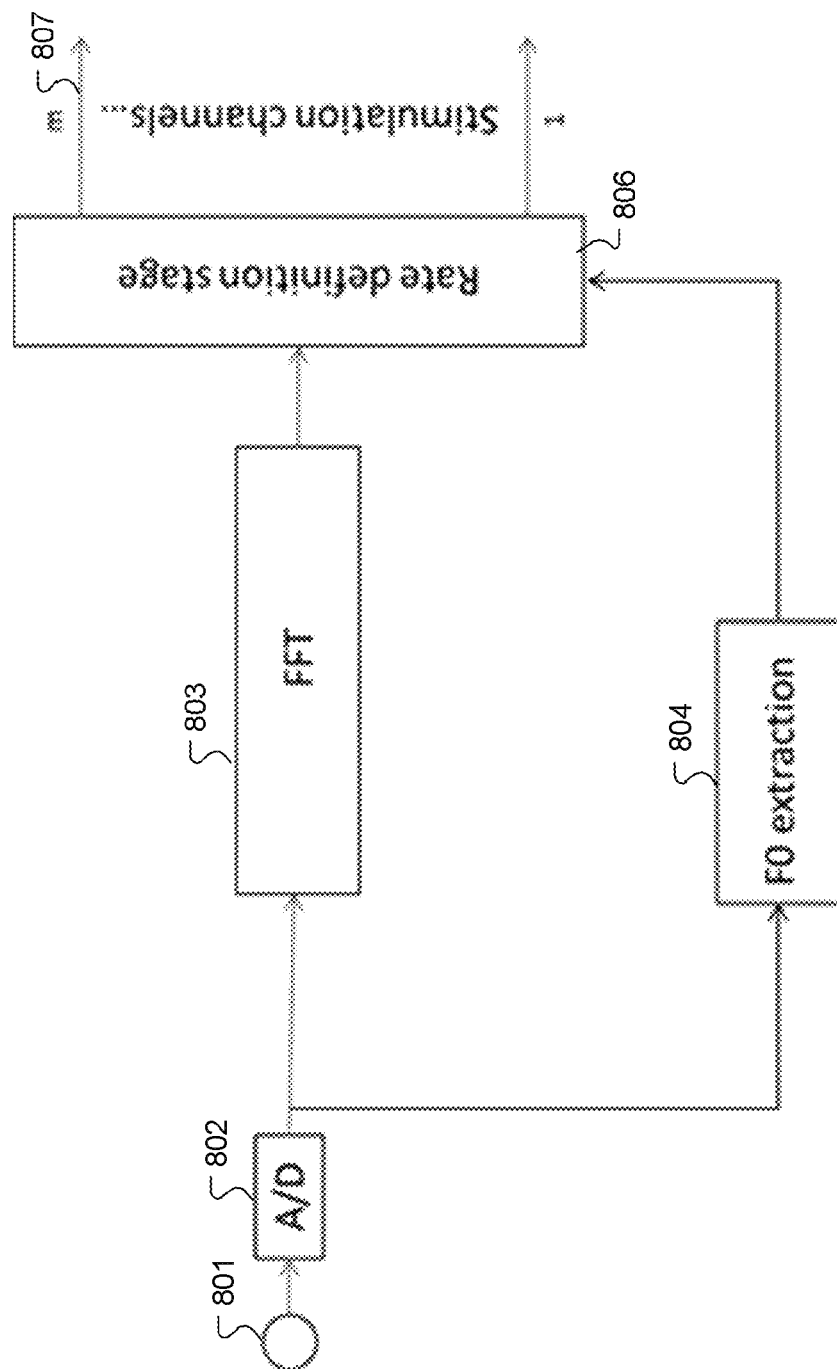
FIG. 8 shows various functional blocks in a feature extraction system in the frequency domain according to an embodiment of the present invention.
Figure 9:
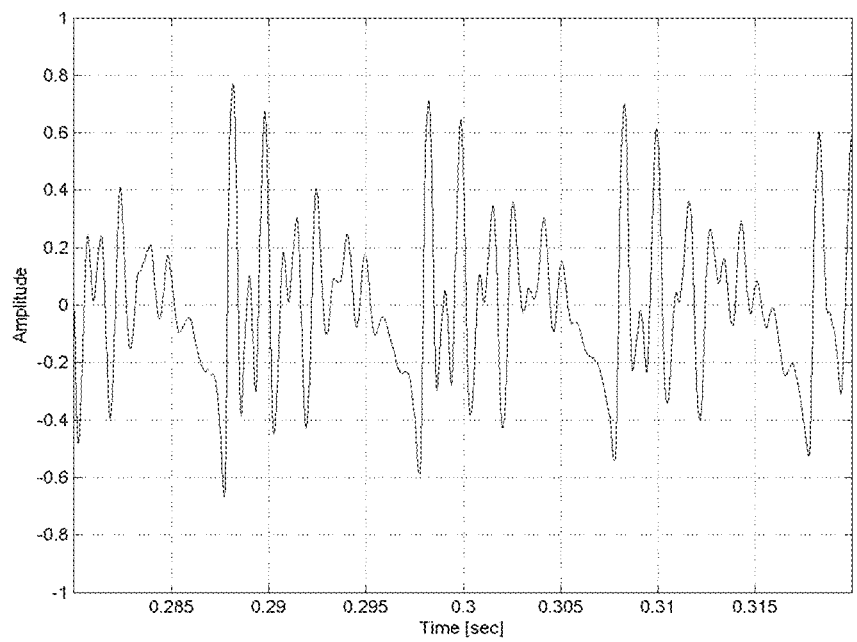
FIG. 9 shows an example of a short time period of an audio speech signal from a microphone.
Figure 10:
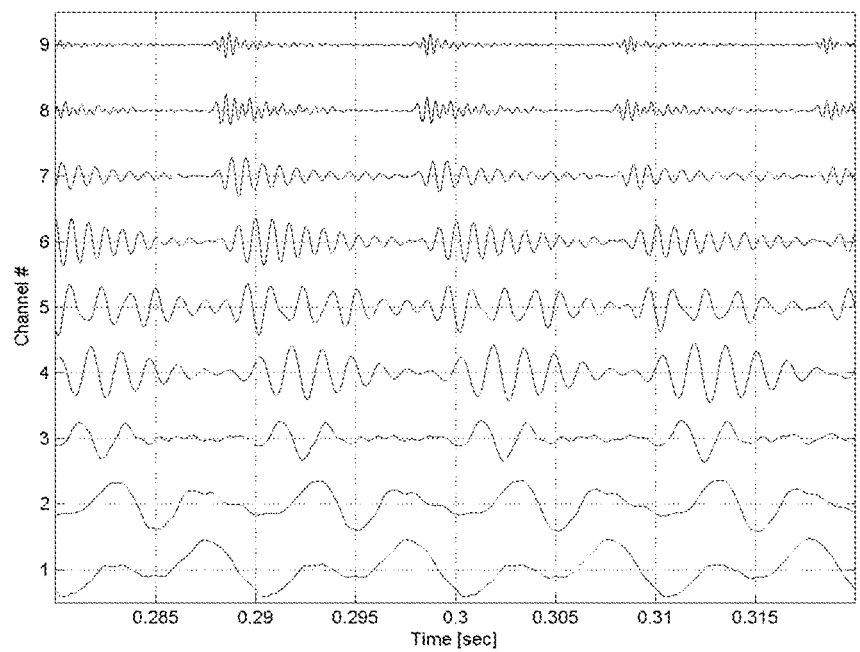
FIG. 10 shows an acoustic microphone signal decomposed by band-pass filtering by a bank of filters into a set of signals.

FIG. 8 shows various functional blocks in a feature extraction system that operates in the frequency domain according to an embodiment of the present invention. For example, this may be based on using a Fast Fourier Transformation (FFT) module 803 rather than the feature counters 705 of FIG. 7. In such an arrangement, the FFT module 803 determines the FFT spectrum of the A/D converted input audio signal. The rate definition stage 806 then determines all signal frequencies of the spectrum with a peak greater than a some predefined value, and calculates the corresponding adjusted feature period for each of the selected signal frequencies. These signal periods may be considered as the feature periods described above with regards to FIG. 6, and then processing continues similarly. Other specific embodiments could be based on a combination of the signal processing arrangements shown in FIGS. 7 and 8 utilizing both time domain feature counters and frequency domain FFT spectrums to determine the feature periods of band pass signals.

One advantage of such as those described above based on language-specific fundamental periods is that the natural preferred periods in tonal languages are better represented, which leads to a better comprehension of speech in tonal languages. In particular, it may be especially helpful for hearing situations with a single speaker where a language-specific fundamental period may be determined very reliably, such as during phone calls in silent environments. But such embodiments may also be helpful in other hearing situations where multiple people may be speaking at the same time by considering directional microphone characteristics. In that case, representation of the speech of a targeted speaker may be enhanced while other voices are attenuated. In hearing situations where detection of a fundamental period may not be reliable enough, the system may switch to another processing mode or the previous selected stimulation rate may be maintained.

Figure 11:
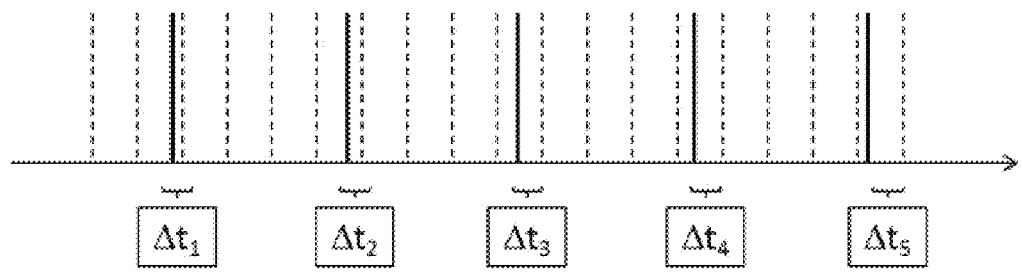
FIG. 11 illustrates the problem of varying jitter between stimulation signals and sensing pattern.

As discussed above, besides language-specific considerations of stimulation rate, representation of the periodicity in an analog signal by a discrete system also is inherently limited by its temporal resolution. For cochlear implants, this means that the highest stimulation rate (which is usually also the highest sensing rate) is the limit for the temporal resolution. If the sensed sound signal has a periodicity with a frequency $f(a)$ and the sensing/stimulation rate of the CI system has a frequency $f(e)$, a beating characterized by both frequencies is generated. Consequently, the electrical pulses may carry a jitter with respect to the zero crossing events. FIG. 11 illustrates this problem of the varying jitter between stimulation signals (solid lines) and sensing pattern (dashed lines). One way to reduce the problem of such jitter is to increase the sensing/stimulation rate. But that is rather energy consuming and ultimately has other technical limitations.

Embodiments are directed to reducing or eliminating unwanted jitter in auditory prostheses such as cochlear implants. In a CI signal processing system such as the ones described above, the signal processing arrangement varies the stimulation frequency for at least one of the electric stimulation signal channels to maintain an integer ratio between the stimulation frequency and the prominent sensed frequency of the corresponding frequency band signal. That is, for at least one of the electrode stimulation channels, the sound processing arrangement changes the sensing/stimulation rate $f(e)$ from a fixed one to a variable one such that it is in an integer relation to the prominent sensed frequency $f(a)$, i.e. $f(e)=n$ times $f(a)$ where n may be an integer or a quotient of integers.

The prominent sensed frequency $f(a)$ may be without limitation the fundamental frequency, a harmonic of the fundamental frequency or simply the most prominent frequency of a pre-defined band filter such as from a low frequency broadband filter as described, e.g., in U.S. Patent Publication 2009/0254150, which is incorporated herein by reference. A broadband coherent mixing arrangement as described in U.S. Patent Publication 2009/0254150 may be advantageous as compared to a system based on determining the fundamental frequency of a frequency band signal since it may be very difficult in many real-life hearing situations to unambiguously determine a fundamental frequency. Alternatively or in addition, the prominent sensed frequency may also be determined via performing an FFT of the sensed signal.

In some embodiments, multiple stimulation signal channels may have their stimulation frequency varied to maintain an integer ratio between the stimulation frequency and the prominent sensed frequency of the corresponding frequency band signals. This may be especially useful, for example, in situations when a cochlear implant user listens to sounds that carry a well-defined fundamental frequency and corresponding harmonics as when listening to music. Thus embodiments of the present invention include cochlear implant systems which have a music processing mode in which the stimulation frequency may be varied to eliminate jitter, and which may be user selectable or automatically selected by the system when appropriate. If the cochlear implant user is in a situation where the system cannot reliably detect a prominent sensed frequency, the system may just switch to another normal stimulation mode and/or a previously selected stimulation rate may be maintained.

Figure 12:
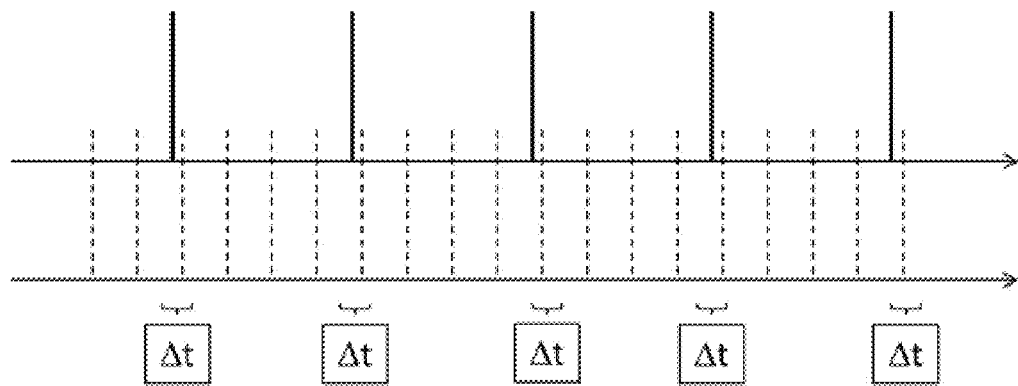
FIG. 12 illustrates stimulation signals and sensing pattern with a constant time offset without jitter as produced by an embodiment of the present invention.
Figure 13:
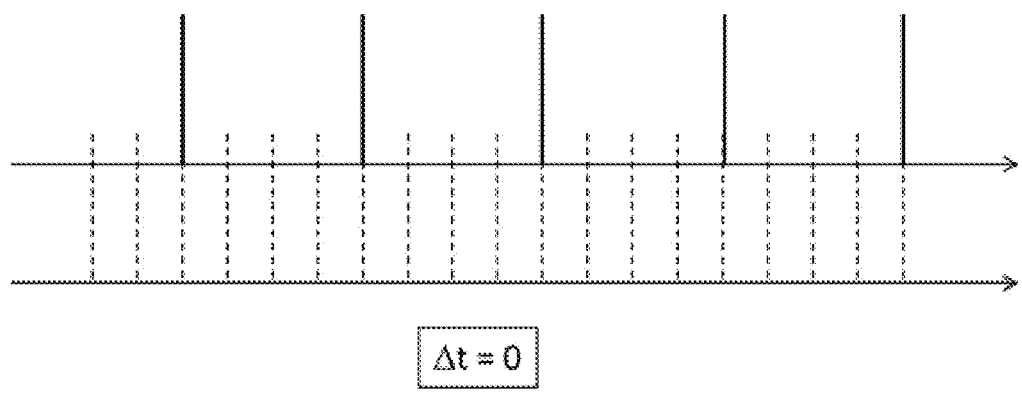
FIG. 13 illustrates stimulation signals and sensing pattern with zero time offset without jitter as produced by an embodiment of the present invention.

Varying the stimulation frequency as described above effectively eliminates the jitter seen in FIG. 11. As shown in FIG. 12, the stimulation frequency can be varied to maintain a constant duration offset between the stimulation signal (solid lines) and the prominent sensed frequency (dashed lines). Or as shown in FIG. 13, an embodiment may control the stimulation frequency with respect to the prominent sensed frequency to have zero offset, and inherently thereby, zero jitter.

One advantage of embodiments of the present invention is that the prominent sensed frequency signal which determines the stimulation rate is more pronounced while other pattern frequencies that may be present in the sensed signal are less represented. So this approach to controlling jitter also introduces a filter for the signal of interest. This may be helpful in some situations such as where multiple people are speaking at the same time. And if a cochlear implant system utilizes directional microphone characteristics, the representation of a targeted speaker's voice may be enhanced while the other speaker voices are attenuated. Thus some embodiments of the present invention may have a target audio source processing mode for such circumstances that eliminates jitter and enhances the prominent frequency of the targeted speaker.

In addition, elimination of unwanted jitter as described above also may be useful or necessary for further processing in specific systems which introduce intentional jitter such as described in U.S. Patent Publication 2008/0319509 and U.S. Patent Publication 2014/0121725, which are incorporated herein by reference.

Embodiments of the invention may be implemented in part in any conventional computer programming language. For example, preferred embodiments may be implemented in a procedural programming language (e.g., "C") or an object oriented programming language (e.g., "C++" or Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve at least some of the advantages of the invention without departing from the true scope of the invention. For example, the approaches described herein could be applied for auditory prostheses other than cochlear implants such as an auditory brainstem implant with the electrical stimuli presented by electrodes within or adjacent to the cochlear nucleus, or an auditory midbrain implant with the electrical stimuli presented by electrodes on or within the inferior colliculus.

What is claimed is:

1. A method for generating electrical stimulation signals for stimulation contacts in an auditory implant system, the method comprising:
    determining characteristic feature periods for a plurality of frequency components in an input audio signal;
    for a plurality of selected feature periods that meet a period selection criteria, determining adjusted feature periods that correspond to a nearest integer multiple of a language-specific fundamental period;
    determining a corresponding stimulation pulse rate for each adjusted feature period as a function of the nearest integer multiple of the language-specific fundamental period;
    assigning each stimulation pulse rate to one or more stimulation contacts; and
    generating the electrical stimulation signals for the stimulation contacts at their respective stimulation pulse rates.

2. The method according to claim 1, wherein the input audio signal is processed using a band pass filter bank to produce a plurality of band pass frequency signals, and wherein characteristic feature periods are determined for each of the band pass frequency signals.

3. The method according to claim 1, wherein the input audio signal is processed using a Fast Fourier Transformation.

4. The method according to claim 1, wherein the frequency components are fundamental frequency components of the input audio signal.

5. The method according to claim 1, wherein the frequency component are harmonic frequency components of the input audio signal.

6. The method according to claim 1, wherein the language-specific fundamental period is characteristic of a tonal language.

7. The method according to claim 1, wherein the language-specific fundamental period is 0.4 milliseconds.

8. An auditory implant system comprising:
    an implanted electrode array having a plurality of stimulation contacts for electrical stimulation of adjacent neural tissue;
    a frequency feature processing module configured for determining characteristic feature periods for a plurality of frequency components in an input audio signal;
    a rate definition stage configured for:
        i. determining for a plurality of selected feature periods that meet a period selection criteria, adjusted feature periods that correspond to a nearest integer multiple of a language-specific fundamental period,
        ii. determining a corresponding stimulation pulse rate for each adjusted feature period as a function of the nearest integer multiple of the language-specific fundamental period,
        iii. assigning each stimulation pulse rate to one or more stimulation contacts, and
        iv. generating output stimulation signals for the stimulation contacts at their respective stimulation pulse rates.

9. The system according to claim 8, wherein the frequency feature processing module includes a band pass filter bank configured for producing a plurality of band pass frequency signals, and wherein the stimulation rate module is configured for determining characteristic feature periods for each of the band pass frequency signals.

10. The system according to claim 8, wherein the frequency feature processing module is configured for using a Fast Fourier Transformation to process the input audio signal.

11. The system according to claim 8, wherein the frequency components are fundamental frequency components of the input audio signal.

12. The system according to claim 8, wherein the frequency component are harmonic frequency components of the input audio signal.

13. The system according to claim 8, wherein the language-specific fundamental period is characteristic of a tonal language.

14. The system according to claim 8, wherein the language-specific fundamental period is 0.4 milliseconds.

* * * * *